United States Patent [19]

Christensen

[11] Patent Number: Plant 5,556

[45] Date of Patent: Sep. 10, 1985

[54] HYBRID TEA ROSE CV. AROCOMU

[75] Inventor: Jack E. Christensen, Ontario, Calif.

[73] Assignee: Armstrong Nurseries, Inc., Ontario, Calif.

[21] Appl. No.: 557,893

[22] Filed: Dec. 5, 1983

[51] Int. Cl.[3] ..... A01H 5/00

[52] U.S. Cl. ..... Plt./11

[58] Field of Search ..... Plt./11

*Primary Examiner*—James R. Feyrer

*Attorney, Agent, or Firm*—Synnestvedt & Lechner

[57] ABSTRACT

A new hybrid tea rose for cut flowers and garden decoration, having as its seed parent Angel Face (U.S. Plant Pat. No. 2,792) and as its pollen parent Double Delight (U.S. Plant Pat. No. 3,847). The new cultivar produces an abundance of well-formed flowers having unusual blended colorations of lavender pink, and having an extremely strong, pleasing fragrance. It is a medium-height, bushy plant that is attractive in the garden.

1 Drawing Figure

This invention relates to a new class of Hybrid Tea Rose cv. Arocomu. The plant is a hardy, outdoor seedling of the medium-height bush type, cultivated for garden decoration. It was propagated by Jack E. Christensen in Ontario, Calif., having as its seed parent Angel Face (U.S. Plant Pat. No. 2,792) and as its pollen parent Double Delight (U.S. Plant Pat. No. 3,847).

The new rose plant cv. Arocomu is particularly characterized by the following combination of characteristics: its unusual blended colorations of lavender-pink flowers, essentially as described and illustrated; its extremely strong and pleasing fragrance; and its abundant production of well-formed flowers. It is a medium-height, bushy plant that is attractive in the garden. It holds these distinguishing characteristics through succeeding propagations by budding.

This new rose may be distinguished from its seed parent Angel Face (U.S. Plant Pat. No. 2,792) by the following combination of characteristics: Angel Face produces flowers of a deep lavender coloration, whereas the new rose produces flowers of a lighter lavender-pink coloration, essentially as described and illustrated herein. Angle Face is classified as a hybrid floribunda rose, whereas the new rose is classified as a hybrid tea. Arocomu produces flowers of a 4- to 5-inch diameter, whereas Angle Face produces significantly smaller flowers of 3½ to 4 inches in diameter.

The new cultivar rose Arocomu may be distinguished from its pollen parent Double Delight (U.S. Plant Pat. No. 3,847) by the following combination of characteristics: Double Delight produces flowers that begin as a creamy white and blush to red, whereas the new rose produces flowers that begin as lavender pink and blush to ruby, essentially as described and illustrated herein. Whereas the new seedling usually produces flowers with 28 to 35 petals, Double Delight bears flowers of a significantly higher petalage (35 to 45). Double Delight does not produce hips under Ontario, Calif. growing conditions, whereas the new rose will set hips under similar conditions.

FLOWERS

The new variety bears its flowers singly, sometimes 2 to 4 flowers per stem in irregular, rounded clusters, on normal strength stems that are of medium length for the class. Outdoors, the plant blooms nearly continuously and in abundant quantities during the growing season. It has a penetrating, strong damask-to-fruity fragrance.

The accompanying drawing illustrates the plant in color and shows the flowering thereof from bud to full bloom.

Throughout this specification, color names beginning with a small letter signify that the name of that color as used in common speech is aptly descriptive. Color names beginning with a capital letter designate values based upon The R.H.S. Colour Chart of The Royal Horicultural Society in London, England.

BUD

The peduncle is of average length for the class and with average caliper, strong and erect. It is moderately smooth with some stipitate glands and beteen Yellow-Green 144A and Green 131A in coloration.

Before the calyx breaks, the bud is medium in size for the class and of medium length, pointed to ovoid in form, with few stipitate glands on the surface of the bud. There are usually slender foliaceous parts extending beyond the tip of the bud equal to one-quarter or more of its length.

As the calyx breaks, the bud color is between Red 53C and Red-Purple 59B.

The inner surface of the sepals has a fine, woolly tomentum; margins are lined with stipitate glands and hairs.

As the first petal opens, the bud is average in size for the class, of medium length and pointed to ovoid in form. The color on the outside has a basal attachment zone near Yellow 1D which quickly suffuses to between Red-Purple 62C and Red-Purple 65C. Any area exposed to sunlight can blush as deeply as between Red 53C and Red 53A. The color on the inside has a basal attachment zone near Yellow 1C which quickly suffuses to between Red-Purple 62D and Red-Purple 65C. Any area exposed to sunlight can blush as deeply as between Red 53D and Red 53A. The bud opens up well and is not retarded or prevented from opening by cold, hot, wet, or dry weather.

BLOOM

The size of the bloom when fully open is average to large for the class, ranging from 4 to 5 inches. The petalage is double, with from 28 to 35 petals and from 3 to 5 petaloids; the petals are arranged regularly. The bloom form when half open is moderately high-centered. The petals are spiraled with the petal edges somewhat reflexed outward. When fully open, the bloom is moderately cupped with petals loosely cupped Petal edges are slightly reflexed outward to flat.

The petals are of moderate substance, of medium thickness and with the inside slightly satiny and the outside slightly shiny. The outside petals are nearly round to broadly ovate, with a rounded apex. The intermediate petals are nearly round to broadly ovate with a rounded to flat apex. The inside petals are broadly ovate and with a flat apex. The colors may be modified by being blotched or shaded or washed or tinted with other colors.

The paragraph immediately following describes the color values observed in a flower newly opened in the month of May. The plant described had been grown outdoors in Ontario, Calif.

The outside surface of the outside petals has a basal attachment zone near Yellow 1D, and the remainder of the petal quickly suffuses to between Red-Purple 62C and Red-Purple 65C; any area exposed to sunlight blushes as deeply as Red 53C and Red 53A. The outside surface of the intermediate and inner petals has the same color as the outside surface of the outside petals but does not blush upon exposure to sunlight. The inside surface of the outside petals has a basal attachment zone near Yellow 1D which quickly suffuses to between Red-Purple 62D and Red-Purple 65C; any area exposed to sunlight blushes as deeply as between Red 53C and Red 53A. The inside surface of the intermediate petals has the same coloration as the inside surface of the outside petals but blushes much less upon exposure to sunlight. The inside surface of the inner petals has the same coloration as the inside surface of the outside petals but does not blush upon exposure to sunlight.

The paragraph immediately following describes color values observed in a bloom which had been open for three days in the month of May. The plant described had been grown outdoors in Ontario, Calif.

The outside surface of the outside and inside petals has a basal attachment zone near Yellow 4C, and the remainder of the petal quickly suffuses to between Red-Purple 65C and Red-Purple 69D. Any area of the outside surface of the outside petal exposed to sunlight blushes as deeply as Red-Purple 57D and Red 53B. Little, if any, blushing occurs on the outside surface of the inside petals. The inside surface of the outside and inside petals has a basal attachment zone near Yellow 4C, and the remainder of the petal quickly suffuses to between Red-Purple 65D and Red-Purple 69D; any area exposed to sunlight blushes as deeply as Red-Purple 57D and Red 53B.

The general color effect of the newly opened flower is between Red-Purple 62D and Red-Purple 65C. The outer petals blush as deeply as between Red 53C and Red 53A. After being open three days, the bloom gives a general color effect which is between Red-Purple 65D and Red-Purple 69D. Most petals blush as deeply as between Red-Purple 57D and Red 53B. The petals usually drop off cleanly and are not particularly affected by cold, hot, or dry weather.

In May, roses grown in the garden last on the bush from 3 to 4 days; cut roses grown outdoors and kept at living-room temperatures will last from 4 to 5 days.

REPRODUCTIVE ORGANS

An average number of stamens are arranged regularly about the pistils.

The filaments are short to medium in length. Most have anthers.

The anthers are small to medium in size, and all open approximately at once. Their color when immature is near Yellow 11B and near Greyed-Orange 177D when mature.

Pollen is moderate in quantity and near Yellow 11B in color.

Pistils are average to many in number (approximately 90).

The styles are uneven, short to average in length, of average caliper, and somewhat loosely bunched.

The stigma is near Yellow 4D in color.

Ovaries are usually enclosed in the calyx.

Hips are of short to average length and globular in shape. Their color is near Yellow-Orange 21D. Hips are moderately smooth with thick, fleshy walls.

Sepals fall soon.

Seeds are average in number (10 to 15) and of small to medium size.

FOLIAGE

The compound leaves are borne in normal to abundant quantities and usually comprise from three to five leaflets. The leaves are of medium size for the class, are moderately heavy and semi-glossy. The leaflets are nearly oval to ovate in shape and have an acute apex and a round base. The margin is simply serrate.

The mature foliage displays upon its upper surface a color which is between Yellow-Green 147A and Green 131A. The under surface is between Yellow-Green 147B and Green 139C.

The upper surface of the young foliage is between Greyed-Purple 183A and Red-Purple 59A. Its under surface is between Greyed-Purple 187A and Red-Purple 59A in color.

The rachis is average to heavy in size, grooved on its upper side, with few stipitate glands on the edges. The underside is sparsely prickly and has few stipitate glands.

The stipules have finely serrated edges and are medium to long in length, of medium width with moderately long points, usually turning out at an angle of more than 45 degrees.

The plant displays an average resistance to mildew and rust as compared to other commercial varieties grown under comparable conditions in Ontario, Calif.

GROWTH

The plant is of medium height, bushy and upright to spreading in habit, and is much branched. It displays vigorous growth. The canes are of medium caliper for the class.

The main stems are between Yellow-Green 146C and Green 139B in color. They bear few to several large prickles which are of medium length for the class. These are almost straight, angled slightly downward, and have a moderately long, narrow base. Their color is near Greyed-Orange 166B. There are no small prickles or hairs on the main stems.

The branches are of a color between Green 137A and Green 136A. They bear few to several large prickles, which are of medium length for the class. The large prickles are almost straight, angled slightly downward, and have a moderately long, narrow base. They are near Greyed-Yellow 161A in color. The branches have no hairs and few small prickles of a near Greyed-Yellow 161A coloration.

New shoots are between Green 137A and Green 136A in color, washed heavily with near Greyed-Purple 187A. They bear several large prickles, which are of medium length for the class. The large prickles are almost straight and angled slightly downward; they have a moderately long and narrow base. Prickle color is near Greyed-Purple 185B. New shoots have no hairs and few small prickles, near Greyed-Purple 185B in color.

I claim:

1. A new and distinct variety of rose plant of the hybrid tea class, substantially as herein shown and described, being particularly characterized by its unusual blended colorations of lavender-pink flowers, essentially as described and illustrated; its extremely strong and pleasing fragrance; its abundant production of well-formed flowers; and by its being a bushy plant of medium height that is attractive in the garden.

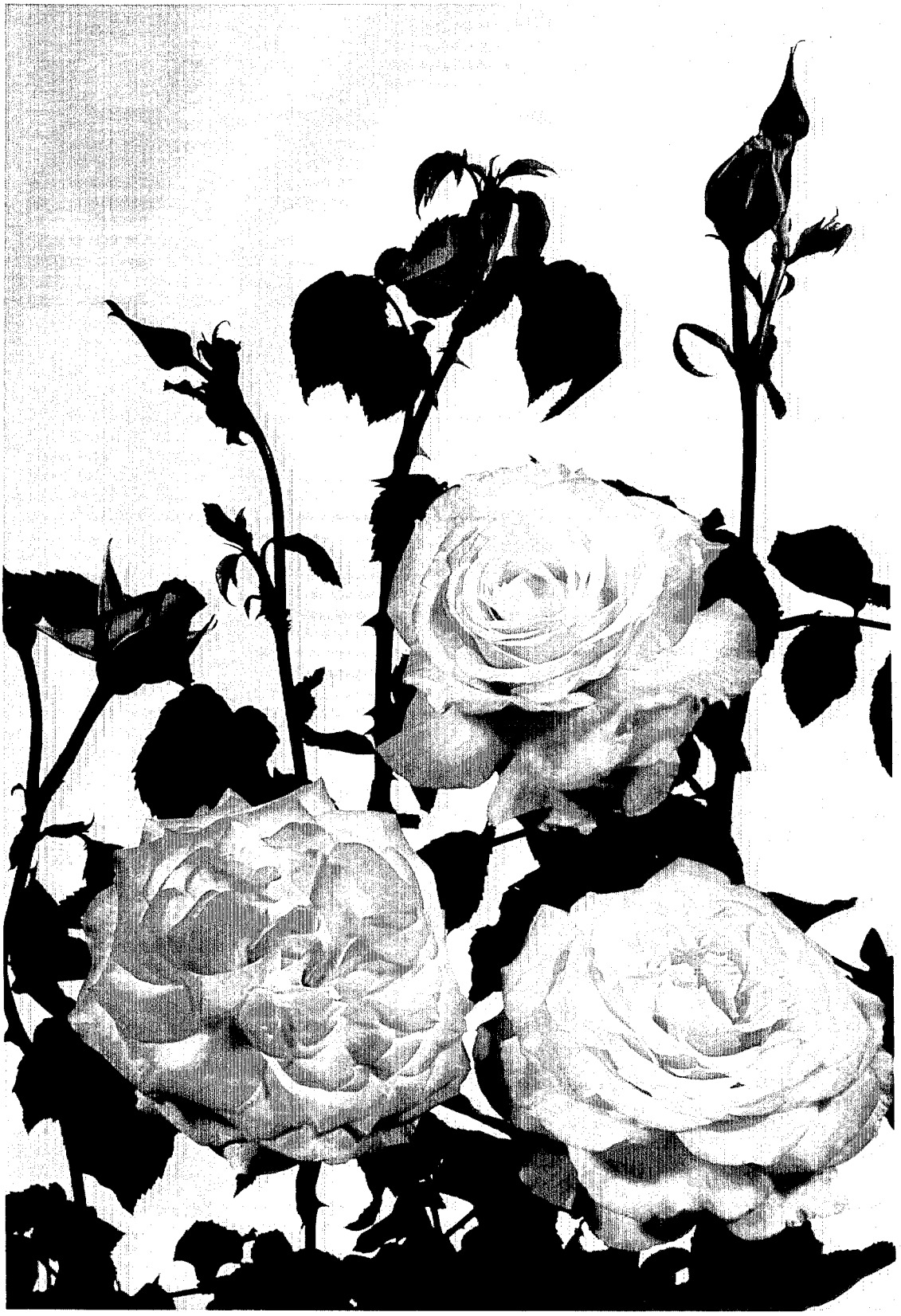

* * * * *